United States Patent [19]
Andersson et al.

[11] Patent Number: 5,497,336
[45] Date of Patent: Mar. 5, 1996

[54] SCANNING DEVICE FOR USE IN MANUFACTURING IMPLANTS

[75] Inventors: Matts Andersson, Lerum; Lennart Carlsson, Mölndal, both of Sweden

[73] Assignee: Nobelpharma AB, Goteborg, Sweden

[21] Appl. No.: 967,616

[22] Filed: Oct. 29, 1992

[30] Foreign Application Priority Data

Nov. 1, 1991 [SE] Sweden .................................. 9103204

[51] Int. Cl.$^6$ .................................................. G05B 19/18
[52] U.S. Cl. .................................. 364/474.03; 364/474.37
[58] Field of Search .......................... 364/474.03, 474.05, 364/474.37, 550, 551.01, 551.02, 559–563; 318/578; 33/503, 516, 505, 504, 23.01–23.09

[56] References Cited

U.S. PATENT DOCUMENTS

| | | | |
|---|---|---|---|
| 4,084,244 | 4/1978 | Floter | 318/578 |
| 4,394,608 | 7/1983 | Tryber et al. | 318/578 |
| 5,003,484 | 3/1991 | Vollmayr | 364/474.03 |
| 5,184,306 | 2/1993 | Erdman et al. | 364/474.05 |
| 5,193,282 | 3/1993 | Aramaki et al. | 364/474.03 |
| 5,204,824 | 4/1993 | Fujimaki | 364/474.03 |
| 5,224,049 | 6/1993 | Mushabac | 364/474.05 |
| 5,283,509 | 2/1994 | Matsuura et al. | 364/474.03 |
| 5,313,400 | 5/1994 | Tsukamoto | 364/474.03 |

*Primary Examiner*—James P. Trammell
*Attorney, Agent, or Firm*—Pollock, Vande Sande & Priddy

[57] ABSTRACT

A scanning apparatus for controlling tool equipment used in production of implants, including a sensing device for sensing a contour of a model to obtain a selected representation based on the sensed contour, processing and controlling devices for receiving and processing the representation signals and for generating a signal array used for controlling of the tool and for controlling the sensing device so that the selected representation signals will ensure generation of the signal array allowing a high degree of accuracy in performance of the controlled tool equipment, wherein the sensing device includes a first device which is interactable with the contour and which displays, at its part interactable with the contour, a first form which substantially corresponds to a second form of a second device included in the tool equipment, with the first and second forms being substantially spherical.

26 Claims, 2 Drawing Sheets

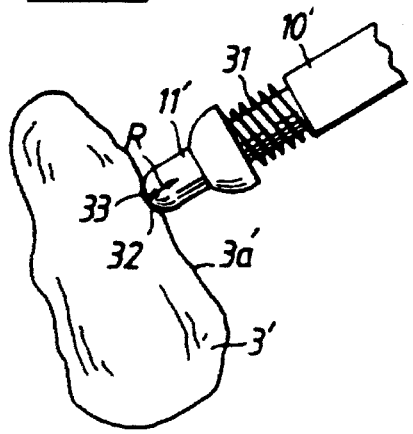
Fig. 2
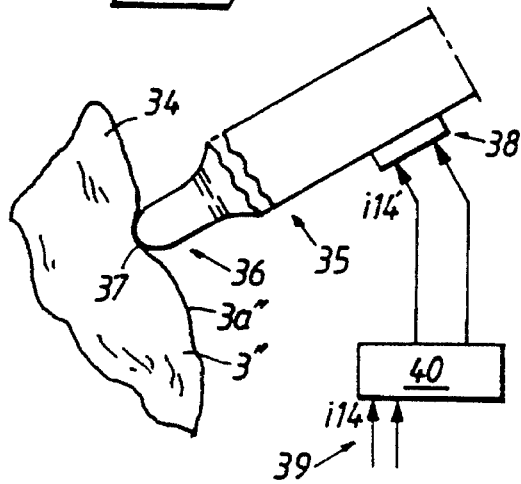
Fig. 3
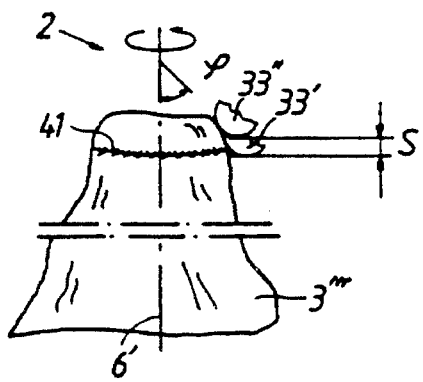
Fig. 4
Fig. 5
| IS | Z | φ° | V | US |
|---|---|---|---|---|
| → | S0/360° | 0° | 100110010111 | ← |
| → | S1/360° | 1° | 110101010101 | ← |
| → | S2/360° | 2° | 111011101111 | ← |
| → | S3/360° | 3° | 110100010110 | ← |
| → | S4/360° | 4° | 111101001001 | ← |
| → | —"— | —"— | —"— | ← |
| → | —"— | —"— | —"— | ← |
| → | —"— | —"— | —"— | ← |
| → | S360/360° | 360° | 110110111101101 | ← |

SCANNING DEVICE FOR USE IN MANUFACTURING IMPLANTS

TECHNICAL FIELD

The present invention relates to a device for generating, by means of scanning applied to a scannable contour on a model, a representation which may be used for controlling a tool which operates with a high degree of precision in connection with the production of a body, or a tool for such a body, which is to be implanted in a human being. As examples of such bodies, mention may be made of dental implants, support members, and the like. The model preferably consists of a three-dimensional model.

BACKGROUND OF THE INVENTION

It is known in the art, in the production of replacement parts, support members and the like in the human body, to utilize a copy milling cutter in which a model is applied and sensed in the cutter and in response to the sensing a tool processes a blank in order to produce from the blank a body or a tool part with the same shape as the model.

Our Swedish patent application No. 9003967-8 corresponding to U.S. Ser. No. 805,955 describes a system in which the sensing or scanning of the model is separate from the processing equipment and control signals for the latter are generated with the aid of computer equipment.

The use of copy milling cutters has its limitations regarding production speed. Moreover, these is an additional disadvantage in that the read-off function and processing function must be located in the same premises. The appearance of the model is strictly linked to the structure of the copy milling cutter, which means that variations and additions to the shape of the model in question, enlargements of the contours and the like cannot be put into effect with the desired freedom of choice.

In connection with equipment in which it is desired that the sensing and processing functions be located in different premises, it is important that an expedient read-off function and processing of the thus obtained representation is effected. The representation and the control must be capable of co-ordination so that unambiguous scanning and sensing can be adapted to an optimum or to the greatest possible extent minimized control signal function.

The quantity of read-off data/information should be kept to a minimum so that the processing and selection functions in the computer equipment may be simplified/reduced while retaining the accuracy of control. The scanning and sensing principles and storage function in the data processing equipment are therefore of crucial importance in this context.

In the case when a telecommmmunications medium (for example, communication via the public telephone network) is to be employed to transmit information from one place to another, it is vital that the quantity of requisite control signals can be reduced. In addition to operating with small scanning and processing quantities, it may be relevant to extract by means of data processing equipment characteristic parts of the read-off information and to transmit these characteristic parts via the medium, and also reconstruct replicas on the reception side with the aid of these characteristic parts so that sufficient control signals for the accurate control of the tool equipment can be obtained. In the scanning and sensing with contact devices/sensing signals, it is also essential for the shape of the position in the part co-operating with the contour relate to the shape of that part of the tool by means of which a blank is processed. An optimum relationship leads to significantly reduced read-off and processing information.

It is also esssential for the sensing and control functions to be related to one another without increasing processed data or information in the data processing equipment. A relationship between reading-in and reading-out of information entered in the computer must also be established in such a manner that, for example, the read-off function will be separated from the read-in function so that the processing function can be carried out more quickly than the read-out function.

The tool equipment must, for example in the production of dental implants, bridges, etc., be capable of working to a degree of accuracy/tolerance of one or a few hundredths of a millimeter, (for example, 0.01–0.09 mm). The resolution on scanning may in one embodiment (for example, scanning by laser) be appreciably greater, for example, one or a few thousandths of a millimeter.

SUMMARY OF THE INVENTION

One object of the present invention is to solve the above-outlined problems by providing a novel problem structure of an apparatus in which a representation may be entered into computer equipment which generates a signal array that effectuates or is included in the control of the tool equipment, and the sensing and/or a selection function effectuated by the computer equipment of the representation is or are selected so as to ensure an order of magnitude of the signal array which satisfies the degree of accuracy with which it is expected that the tool equipment will perform.

In one embodiment, the sensing means operates with a first member co-operating with the contour, for example, a needle. At its portion co-operating with the contour, the member displays a first form which substantially corresponds to a second form of a second member which is included in the tool equipment and which interacts, with a portion carrying the second form, with a blank in the production process. The portion may consist of a milling cutter. In one embodiment, the first and second forms are substantially spherical. In addition, the sensing function and the processing function of the tool equipment are mutually co-ordinated so that a linear transmission function arises. The sensing function and the processing function may then operate at different speeds. It is thus of interest in this art that the speed of the processing function may exceed the sensing function.

The computer equipment is preferably designed with memory means in which the representation or information of significance for the representation is stored. The memory may, for instance, consist of a magnetic internal or primary memory of the RAM type. In that case when information is to be stored, a secondary memory may also be employed. Such secondary memory may be of the permanent magnet type. The read-in function of the information is then preferably separated from its read-out function so that, for example, control signal generation may be carried out more rapidly than the read-in of the representation.

In one embodiment, the present invention will comprise a contour sensing portion interactable with the contour and having a curved surface which may be brought into abutment against the surface of the contour. The dimensions of the curved area, for example a spherical area, are to be put into relation with the details of the contour so that a reduced sensing degree (resolution) is obtained.

In one embodiment, the sensing function takes place on models of soft or brittle material, for example plaster. With the aid of the tool equipment, bodies or tool parts may be made completely or partly of hard, soft or brittle material.

In one embodiment, compression takes place in the computer equipment of first information referable to the representation on the formation of second information referable to control of the tool equipment. The first and/or second information may be stored in storage devices on delayed transmission of the control information, for example via a telecommunications medium (for example the public telephone network). The storage devices may then be designed with a capacity which entails storage of the information from sensing of one or more contours. In one embodiment, the storage devices have a capacity of at least 2–3 megabyte.

In one embodiment, the sensing is carried out during rotation of the model with simultaneous mutual relative displacement between the model and a sensing device. The sensing function is executed a large number of times per revolution, for example, 360 times per revolution. The relative displacement may be selected to be approximately 0.1 mm/revolution. Only characteristic parts of the representation and/or control can, in one embodiment, be transmitted on the employed telecommunications medium. A replica of the control/control signals is generated at a reception point with the aid of the characteristic parts.

The present invention also utilizes known mathematical principles in the compression function.

As a result of the proposals disclosed in the foregoing, a considerable reduction may be achieved in the quantity of information which is obtained in the sensing function. The capacity and space on the computer equipment may then be kept to a minimum, at the same time as transmission via the relevant link is simplified/shortened in terms of time. The sensing and control signal-generating functions may be kept separated and processed independently of each other. A plurality of sensing stations may be connected to the same computer equipment and similarly a-plurality of sensing and computer equipment units may be connected to one and the same tool equipment via the same or different connections. The information quantities may be reduced substantially, which gives short processing times in the computer equipment and transmission of a relatively small quantity of control information. The proposed principles also afford the possibility of so-called contact-free sensing in which the sensing function more exactly and in greater detail senses the contour in question. The representation obtained from the sensing function can be reduced/compressed in the computer equipment with the aid of the selection function. As a result of the proposed spherical shape of the abutment portion of the sensing device against the contour, sensing of soft and/or brittle models can be carried out. Since the shapes of the sensing and processing device are designed to be substantially identical, complicated calculated functions referable to the actual and sensed contour of the model in question are eliminated. As a result of the proposed structure, the processing capacity in the computer equipment may be reduced by one third and savings of the space/volume of the computer equipment may be reduced by up to one fifth.

BRIEF DESCRIPTION OF THE ACCOMPANYING DRAWINGS

One currently preferred embodiment of an apparatus which displays the characteristic features of the present invention will be described in greater detail hereinbelow, with particular reference to the accompanying Drawings, wherein FIG. 1 shows in a block diagram form the structure of the sensing device with computer equipment (PC), programmable input and output circuits, control unit for signal emission and signal sensing units in which the signal emitting unit controls a model carrying unit so that this moves in relation to a sensing unit that emits signals to the signal sensing unit;

FIG. 2 shows, on a larger scale and from the side, how a sensing portion in a sensing unit interacts with the contour of a model;

FIG. 3 shows from the side how a blank is processed by means of a tool equipment part, by means of which the contour in FIG. 2 is produced from the blank on reduced, equal or enlarged form;

FIG. 4 shows on a larger scale the interaction between the sensing portion and the contour of the model; and FIG. 5 shows in a table form how the sensing proceeds in the embodiment according to FIG. 4.

DETAILED DESCRIPTION OF EMBODIMENT

Figure 1:
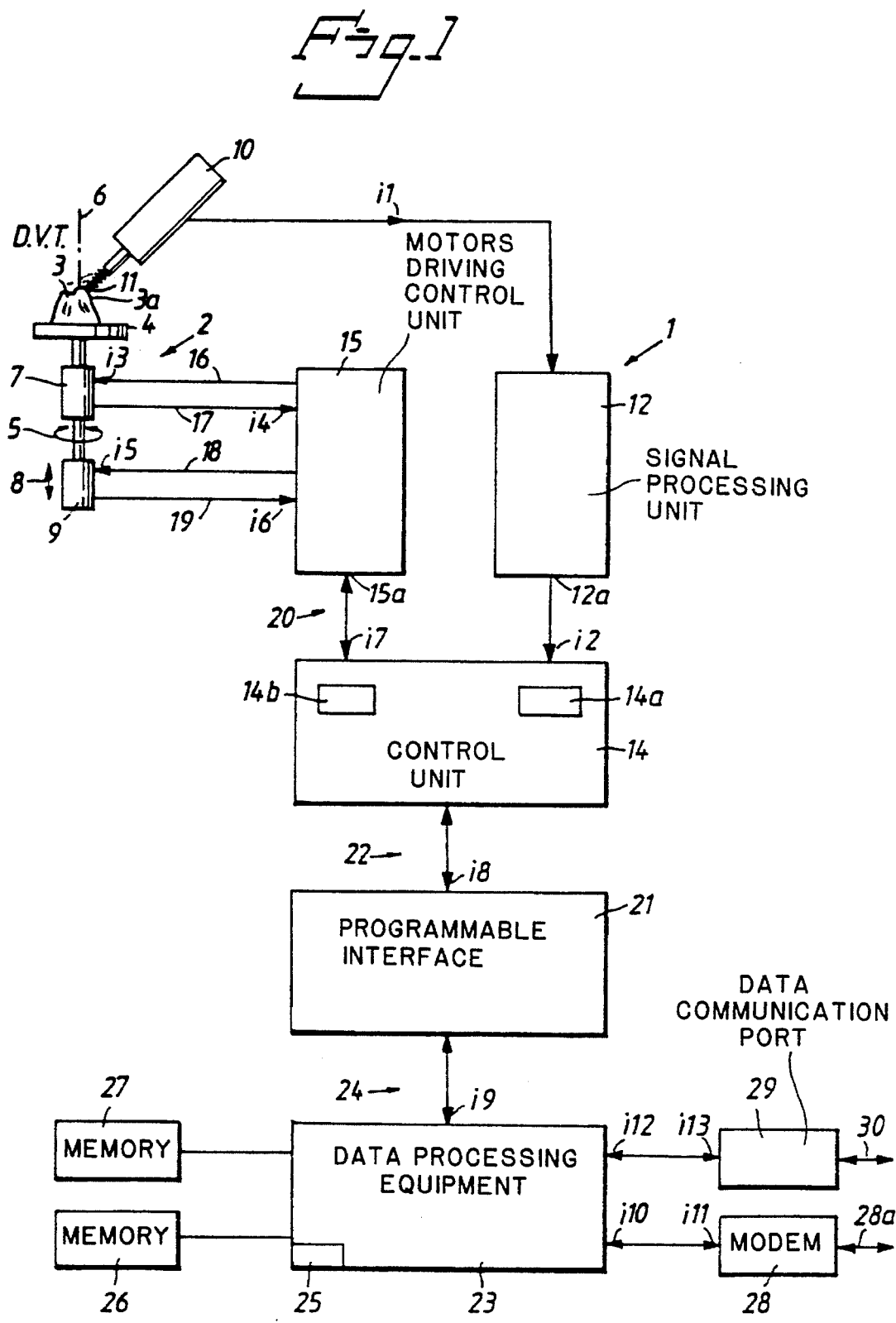

Referring to the Drawings, in FIG. 1 a read-off device is given reference designated as 1 and comprises among other things, a mechanical unit 2 on which a model 3 may be secured on a rotatable device 4. In addition to being rotatable in the direction of the arrows of rotation 5 (counter-clockwise and clockwise) about an axis of rotation 6 by means of a drive motor 7, the device 4 and the drive motor 7 are longitudinally displaceably disposed in the directions 8 of the axis 6. By this means, the model 3 will also be longitudinally displaceably disposed in the directions 8. The longitudinal displacements are realized by means of a motor 9. A sensing unit 10 which is fixedly disposed in relation to the model is provided with a device 11 which may be resiliently brought into contact with the contour 3a of the model 3. When the model is turned and displaced in relation to the unit 10 and the device 11 in connection with the activations of the motors 7 and 9, these will be received from the output of the unit 10 a representation in response to sensing by the device 11 of the contour 3a, the representation being in the form of one or more electric signals i1. The latter signal or signals are processed in a signal processing unit 12 where the representation i1 is sampled and digital signals i2 are obtained from the output 12a of the unit 12 in response to the samplings. The digital signals can be transmitted on a bus connection for parallel transmission of 16 bits. The unit 12 is, via the bus connection, connected to a control unit 14. The motors 7, 9 are controlled by means of a combined unit 15 for driving, speed adjustment and positioning of the motors. The control functions for the motors operate with feedback function and the control and feedback conductors are indicated by reference numerals 16, 17; and 18, 19, respectively, and the set and actual value signals are indicated by i3, i4; and i5, i6, respectively. The unit 15 is connected via inputs and outputs 15a to the control unit 14. The connection is designed as an additional bus connection 20 for 16-bits parallel transmission. The control unit comprises first and second units 14a and 14b which serve units 12 and 15 respectively. Control of the motors 7 and 9 is related to the sensing and the representation i1 for this.

The sensing device includes a programmable interface 21 with read-in and read-out devices which are connected to the control unit 14 via a bus connection 22 for 24-bits parallel transmission. A data processing equipment, for example a PC 23, is connected to the read-in and read-out devices 21 via a bus connection, for example an AT bus connection. The PC may be of AT-286 type which includes one or more magnetic internal memories or primary memories of the RAM type. The computer 23 is also fitted with a secondary memory 26, 27 of the permanent magnet type. A memory 26 may consist of a hard disk and a memory 27 of a floppy disk.

The signals on the bus connection 20 are shown with reference numeral i7, on the bus connection 22 with i8 and on the bus connection with i9. The computer 23 is connected to or provided with a data communication port 28 via which the control/representation information may be entered into and retrieved from the read-off device via an input and output 28a to and from another data processing equipment or data communication (not shown). Moreover, the computer 23 is connected to a modem 29 via which the computer may be connected to a telecommunication connection 30 in a telecommunications network, for example the public telephone network. Information to and from the connection 30 via the modem 29 is indicated by reference numerals i12 and i13 respectively.

The software which is employed in the computer may be of known type. In the present case, the following are employed:
User program
Program for text and calibration
Program for file handling
Program for data compression
Program for data communication
Program for automatic call up/transmission via the modem on the telecommunications network, single/multiple file program.

FIG. 2 shows the device 11' sensing the contour 3a' of the model magnified in relation to FIG. 1. The resilient abutment of the device 11' against the contour is effectuated by spring means 31. The unit 10' is securely disposed in relation to the device 11'. The latter is designed with an abutment portion 32 which is preferably substantially spherical in the illustrated case. The spherical shape is indicated by reference numeral 33.

In FIG. 3, a blank is indicated by reference numeral 34. The blank, which may be of titanium, cemented carbide, alloy, graphite, and the like, must be provided with a contour 3a and 3a' in FIGS. 1 and 2 corresponding to contour 3a'. The blank 34 is processed or treated with a tool 35 which, in the present embodiment, consists of a milling cutter. The forward portion 36 of the tool has a shape 37 which substantially, preferably exactly, agrees with the shape 33 of the read-off device 32 according to FIG. 2. The tool/milling cutter is disposed in a known manner in a spindle and the tool includes a tool adjustment control portion 38 which receives control signals i14 via the telecommunication connection 39 (see 30 in FIG. 1) and a modem 40 which interacts with the modem 29 according to FIG. 1. Via the modem 40, control signals i14' are fed to the control portion 38.

FIGS. 4 and 5 show the read-off principle, read-in and read-out into and from, respectively, the memory of a computes of sensed values and entered values V, respectively. The model 3''' is rotated about its axis 6' and sensing takes place in different angles) ρ. In the example, sensing takes place for each degree, that is, 360 times per revolution and the read-off angles are indicated by 0–360. The read-off points are symbolized by reference numeral 41. For each revolution (360), the model moves in a Z direction in relation to the read-off portion 33', 33'', these positions each representing their location in relation to the model 3'''. For every revolution that the model rotates, a relative movement S (=pitch) between the model and the sensing portion in the present embodiment is 0.1 mm. In the table according to FIG. 5, the pitch Z for each degree ρ is 0.1 mm/360. Other pitches S and number of sensing points may be employed within broad limits.

In the table IS indicates a read-in sequence in the memory of the computer and US a read-out sequence from the memory. V represents read-in/readable value for each degree. The values V occur in binary form or other suitable form. The sequences IS and US can be executed in a known manner at different speeds. The sequence US is preferably higher than the sequence IS.

The sensing surface 33 of the sensing portion 32 displays a radius R which may lie within the range of between 0.5 and 2.0 mm and is preferably 1.0 mm. This size of the radius is suitable in production from models which represent a dental implant, bridge, and the like. The sensing surface 33 is thus selected so as to give a reduced sensing degree/resolution in relation to the true detailed shape of the contour.

One method of compressing the entered data quantity is to approximate a number of points by means of a function, for example, a polynomer of the third degree ($c_1+c_2x+c_3x^2+c_4x^3$). The total computer quantity is divided into groups. Each such group is approximated by a function. So instead of transmitting pure measurement data from the read-off unit to a relevant factory computer, the coefficients of the function are transmitted for each group ($c_2$, $c_2$, $c_3$ and $c_4$ in the case employing a polynomer of each degree).

Since both functional value (indicator signal) and the distance between each read-in is known, that is f (x) and x in each group when the function is a function of a variable, the function may be approximated by the least square method. The solution in the sense of the least square method to the above equation system $Ac=f$ is given by the solution to the equation system $Au^TAc=A^Tf$. If Q(x) is the indicator signal at a given position and $\bar{f}(x)$ is the approximated value at the same point, the error can be calculated with error(x)= f(x)·Q(x). The number of values included in each group to be approximated by a function must be adapted such that the error (error(x)) is less than the largest permitted error for all values in the group. The above mathematical processing is carried out in the computes in a known manner.

The present invention should not be considered as restricted to that described above and shown on the drawings, many modifications being conceivable without departing from the spirit and scope of the appended Claims.

We claim:

1. A scanning apparatus for controlling tool equipment used in production of three-dimensional bodies such as human body restorations, comprising:

sensing means for sensing a contour of a model to obtain selected representation data based on said sensed contour in the form of at least one signal, said sensing means being located at a first site;

movement effecting means for effecting rotational movement of said model simultaneously with relative displacement movement between said model and said sensing means while said sensing means simultaneously sensing the contour of the model, said movement effecting means being actuated and controlled by a control unit;

processing and controlling means for receiving and processing said representation data signals and for generating sensing control signals used for controlling a sensing function of said sensing means;

computer equipment for obtaining input signals based on said processed representation signals and for generating output signals to be used in controlling of said tool equipment;

means for controlling operation of said tool equipment at a second reproduction site;

means for transmitting output signal data from said first site to said second reproduction site.

2. The apparatus as claimed in claim 1, wherein the sensing means and said tool operation controlling means are designed to perform in a substantially coordinated manner.

3. The apparatus as claimed in claim 1, wherein the sensing means and said tool operation controlling means operate at different speeds.

4. The apparatus as claimed in claim 1, wherein an information significative of the representation is storable in a memory of the computer equipment.

5. The apparatus as claimed in claim 4, wherein said memory includes at least one of an internal (primary) memory of the RAM type and a secondary memory of the permanent magnet type, and wherein the reading-in of said information is separated from its reading-out.

6. The apparatus as claimed in claim 1, further comprising means for rotation of the model with simultaneous mutual relative displacement between the model and the sensing means when the sensing means senses the contour, and wherein the sensing takes place a large number of times per revolution.

7. The apparatus according to claim 1, wherein said sensing takes place about 360 times per revolution, and said relative displacement is about 0.1 mm/revolution.

8. The apparatus as claimed in claim 1, wherein the sensing means is connected to the computer equipment via an interference comprising programmable input and output circuits, which are connectable to said processing and controlling means including said control unit which is connected to a signal generation unit for a model movement actuating means and to a unit converting the shape of the contour into electrical signals.

9. The apparatus as claimed in claim 1, wherein the sensing surface of the sensing portion displays a radius (R) in the range of between 0.5 and 2.0 mm to cooperate with a model which represents a dental implant, bridge and the like.

10. The apparatus as claimed in claim 1, wherein said sensing means includes a first device which is interactable with the contour and which displays, at its part interactable with the contour, a first form which substantially corresponds to a second form provided on a second device included in the tool equipment, said first and said second forms being substantially spherical.

11. A scanning apparatus according to claim 1, wherein said sensing means is positioned at an angle with respect to a longitudinal axis of said model.

12. A scanning apparatus according to claim 11 wherein said tool equipment is positioned at an angle with respect to a longitudinal axis of said blank.

13. An apparatus for controlling tool equipment used in manufacturing at least one three dimensional body, comprising:

sensing means including a sensing device for sensing a contour of a model of an implant to obtain a representation of said contour in the form of at least one representation electrical signal;

said sensing means including means for effecting rotational movement of said model simultaneously with relative displacement movement between said model and said sensing device while simultaneously sensing said contour;

a signal processing unit for processing said representation electrical signals to obtain digital signals;

a control unit for controlling operation of said signal processing unit and said sensing means; and data processing equipment for receiving signals from said control unit and for generating control signals used for operating said tool equipment;

wherein said sensing means includes a first member which is interactable with the contour of the model during said sensing and has at its part interactable with the contour of the model a first form which is the same as a second form at a part of a second member provided in said tool equipment which is interactable with a blank in production of said three dimensional body;

wherein said sensing means is inclined at a first angle with respect to a longitudinal axis of said model, said tool equipment is inclined at a second angle with respect to a longitudinal axis of said blank, and wherein said first and second angles of inclination are substantially the same.

14. An apparatus according to claim 13 wherein said first and second forms are spherical.

15. An apparatus according to claim 13, further including a programmable interface including read-in and read-out devices connected between said control unit and said data processing equipment.

16. An apparatus according to claim 15, wherein said data processing equipment includes a computer with at least one primary magnetic memory of the RAM type.

17. An apparatus according to claim 16, wherein said computer is also provided with a secondary memory of a permanent magnetic type.

18. The apparatus as claimed in claim 15, wherein the read-in or read-out data quantity is compressed by means of an approximation of a quantity of read-in or read-out points with a function which is a polynomer of the third degree.

19. The apparatus as claimed in claim 18, wherein the read-in or read-out data quantity is divided into groups; each respective group is approximated with a function; and the coefficients of each respective function are transmitted between relevant communication parts, including from the read-out unit to a computer, at the reproduction site as representation of the total quantity of read-in or read-out data.

20. The apparatus as claimed in claim 19, wherein the error between an actual indicator signal and each respective approximate value is calculated, and also the number of included values in each respective group of said groups which is to be approximated with a function will be adapted such that an absolute value error is less than the largest permitted error for all values in the group.

21. The apparatus as claimed in claim 13, wherein the speed of the processing and controlling units exceeds that of the sensing means.

22. The apparatus as claimed in claim 13, wherein a first information data referable to the representation is compressed in the data processing equipment on formation of a second data information referable to the control of the tool equipment, and wherein at least one of the first and the second information may be storable in a storage means in order to realize a time lag between at least one of the sensing and controlling functions in relation to a transmission of the controlling signals to the data processing equipment.

23. The apparatus as claimed in claim 22, wherein said storage means stores the representations for one or more contours for transmission via a telecommunications medium at off-peak hours thereon, and wherein said storage means have a capacity of at least 2–3 megabyte.

24. The apparatus as claimed in claim 13, wherein the sensing surface of the sensing device is selected to provide a reduced sensing degree/resolution in relation to the true detailed form of the contour.

25. A scanning apparatus for controlling tool equipment used in production of three-dimensional bodies such as human body restorations, comprising:

sensing means for sensing a contour of a model to obtain selected representation data based on said sensed contour in the form of at least one signal;

processing and controlling means for receiving and processing said representation data signals and for generating sensing control signals used for controlling a sensing function of said sensing means;

computer equipment for obtaining input signals based on said processed representation signals and for generating output signals to be used in controlling of said tool equipment; and movement effecting means for effecting rotational movement of said model simultaneously with relative displacement movement between said model and said sensing device while simultaneously sensing the contour of the model, said movement effecting means being actuated and controlled by a control unit; and wherein characteristic parts of the representation and the control are selected prior to the transmission on a telecommunications medium; and wherein a replica is generated at a reception site based on the characteristic parts of the representation.

26. A scanning apparatus for controlling tool equipment used in production of three-dimensional bodies such as human body restorations, comprising:

sensing means for sensing a contour of a model to obtain selected representation data based on said sensed contour in the form of at least one signal;

processing and controlling means for receiving and processing said representation data signals and for generating sensing control signals used for controlling a sensing function of said sensing means;

computer equipment for obtaining input signals based on said processed representation signals and for generating a controlling signals array to be used in controlling of said tool equipment; and movement effecting means for effecting rotational movement of said model simultaneously with relative displacement movement between said model and said sensing device while simultaneously sensing the contour of the model, said movement effecting means being actuated and controlled by a control unit;

and wherein a first information data referable to the representation is compressed in the computer equipment on formation of a second data information referable to the control of the tool equipment, and wherein at least one of the first and the second information may be storable in a storage means in order to realize a time lag between at least one of the sensing and controlling functions in relation to a transmission of the controlling signals to the computer equipment.

\* \* \* \* \*